United States Patent [19]
Serabian-Musto

[11] Patent Number: 5,244,394
[45] Date of Patent: Sep. 14, 1993

[54] DENTAL EDUCATION KIT
[76] Inventor: Judy Serabian-Musto, 437 Birchwood Dr., Berea, Ohio 44017
[21] Appl. No.: 998,002
[22] Filed: Dec. 29, 1992
[51] Int. Cl.$^5$ ............................................. G09B 23/28
[52] U.S. Cl. ................................... 434/263; 434/262; 434/429
[58] Field of Search ............... 434/262, 263, 267, 428, 434/429, 430; 40/630, 638, 594

[56] References Cited
U.S. PATENT DOCUMENTS

| | | | |
|---|---|---|---|
| 3,547,341 | 12/1970 | Kirkpatrick | 229/63 |
| 4,199,145 | 4/1980 | Gouraige | 434/263 X |
| 4,422,852 | 12/1983 | Mathias | 434/178 |
| 4,869,531 | 9/1989 | Rees | 283/67 |
| 4,888,251 | 12/1989 | Nakada | 434/263 |
| 5,015,209 | 5/1991 | Ortiz | 446/73 |
| 5,102,169 | 4/1972 | Mayfield | 283/115 |

Primary Examiner—John J. Wilson
Assistant Examiner—L. Thomas
Attorney, Agent, or Firm—Richard C. Litman

[57] ABSTRACT

An educational dental kit for entertaining and educating young children about both the mythological "Tooth Fairy" and about good dental hygiene. The kit comprises a greeting card, a poster, and a drawstring pouch. The poster portrays a child's face with particular emphasis on the mouth. The teeth on the mouth are printed on removable stickers, each sticker representing a different tooth. When the child loses a tooth, the corresponding sticker is removed from the poster and is placed in the appropriate location on the greeting card. Indicia describing the teeth as well as proper dental hygiene may be located on the poster. The greeting cards may include indicia in the form of an image or text. The greeting cards may also encourage active participation of the child. A number corresponding to the order in which each tooth is lost may also be provided on each greeting card. The numbers would appear in ascending order on each successive greeting card. The first time a tooth is lost, the child should receive the first card. When the second tooth is lost by the child, the second greeting card should be presented, when the third tooth is lost, the third greeting card should be presented, and so on. A drawstring bag is included in the kit to provide a way for the parent to quickly and efficiently locate and retrieve the lost tooth from under the child's pillow.

15 Claims, 5 Drawing Sheets

DENTAL EDUCATION KIT

BACKGROUND OF THE INVENTION

1. Field of the Invention

The present invention relates to educational materials. More particularly, the present invention pertains to a novel teaching accessory that will educate and assist a child in learning more about proper dental hygiene.

2. Description of the Prior Art

Teaching aids, including board games and educational toys have been the subject of patent protection for many years. In the field of dentistry however, very few educational and entertaining devices have been patented. One example of a board game, however, can be found in U.S. Pat. No. 4,199,145 issued Apr. 22, 1980 to G. F. Gouraige, Jr. This patent discloses a dental board game apparatus which can be used as an aid in learning the anatomy of the mouth and the names and positions of the various teeth of the mouth. The game includes a game board, playing pieces which represent the teeth of one quadrant of the mouth, and a die. The purpose of this board game is to provide an apparatus which is both entertaining as well as educational, allowing players to become readily acquainted with dental terminology. However, this game may be too complicated for young children to play or understand. In addition, during a child's formative years, between the ages of four and nine years old, the child should be exposed to good oral hygiene techniques as well as educated about the various parts of the mouth. The present invention overcomes this limitation by providing a device which provides both visual and hands-on learning experience as well as encourages activities which can be shared by the whole family.

Other patents dealing with dentistry, and more particularly with the mythological tooth fairy can be found in U.S. Pat. No. 5,015,209 issued May 14, 1991 to T. Ortiz. Ortiz discloses a child-playing toy with a basic structure of a molar having two butterfly-like wings at its side. The top of the molar represents the head and face of a doll while the two roots of the tooth are its legs. The doll has two arms, one of which carries a wand, and behind the wings there exists a sack or pouch wherein a tooth in which a child has lost may be placed. The article is intended to enable parents to easily retrieve the child's fallen tooth without disturbing the child by having to reach under his or her pillow. The Ortiz invention enables a parent, in the presence of the child, to place a lost tooth in the sack or pouch which is attached to the doll. Cuddling the doll, the child falls asleep. While the child is sleeping, the parent may, on the tooth fairy's behalf, more easily reclaim the tooth from the pouch in exchange for a gift. While the Ortiz patent does provide the parent and child with an entertaining device for exchanging money for a lost tooth, it does not provide any educational value to the child concerning proper oral hygiene or the anatomy of the mouth.

A teaching aid can be found in U.S. Pat. No. 4,422,852 issued Dec. 27, 1983 to E. A. Mathias. This device has an elongated backing including an open slot terminating into a central opening. One end of the aid has a picture of a face imprinted thereon and indicia is printed on the elongated backing. The process for teaching comprises pivoting the teaching aid around a doorknob shaft into a generally horizontal position such that a child can readily read all of the indicia. Arranged educational indicia is printed in a visual presentation form for rapid and comprehensive understanding. Part of the indicia is printed such that it can be read fairly easily when the teaching aid is hung in a generally vertical upright position on the doorknob-shaft combination. While this device is a novel teaching aid, it does not provide the parent or child with a way to interact together while the child learns.

Other prior art patents disclose certain aspects of the present invention. U.S. Pat. No. 3,547,341 issued Dec. 15, 1969 to G. F. Kirkpatrick discloses a drawstring bag with an open mouth defined by tubular channels extending along transverse top edges of front and back walls of the bag. One of the channels has an opening at a first longitudinal edge of the bag and the other channel has an opening at a second longitudinal edge, opposite the first longitudinal edge. A string extends through each channel. One end of each string is attached to the longitudinal edge and the other end of each string protrudes transversely through the respective opening opposite the longitudinal edge. Each string may be pulled in an opposite direction whereby the channels are gathered tightly and regularly and the free ends of the strings are easily tied to each other.

In addition, U.S. Pat. No. 5,102,169 issued Apr. 7, 1992 to M. E. Mayfield discusses a chart utilizing tactile and visual medication symbols and marking elements. The medication marking elements are removably attachable to a chart. These elements may be erasable marks made by a marking pen or pencil. The invention is designed to provide the user with an easy to understand chart for taking multiple medications at varying times.

Another device provides an apparatus and method for documenting the findings of a physical examination. This apparatus can be found in U.S. Pat. No. 4,869,531 issued Sep. 26, 1989 to M. K. Rees. The Rees patent includes a group of pre-printed stickers each having an anatomical designation in either a graphic or text form, on their front surface and an adhesive backed peel-off sheet on their rear surface. The physician or patient can mark directly on the sticker to indicate the location, size and shape of any abnormality on the patient. The sticker may then be removed and attached directly to the patient's progress report.

Although the aforementioned patents teach of devices such as board games, dolls and teaching aids as well as devices such as pull string bags and devices carrying removable stickers, none of the above patents, taken either singly or in combination, is seen to describe the instant invention as claimed.

SUMMARY OF THE INVENTION

By the present invention, an educational and entertaining device overcomes shortcomings in the above mentioned prior art and provides a novel way of giving a child a more intimate connection with his or her parents, knowledge of the anatomy of the mouth, and proper dental hygiene techniques. The method used to achieve these goals consists of a series of greeting cards, a poster to be hung on the wall of the child's room, and a pouch that would be placed under the child's pillow on the occasion of the loss of one or more of their teeth. The poster has detachable stickers, each of which represents individual tooth. As a child's tooth is lost, a sticker can be removed from a location on the poster and placed onto a designated area on one of the series of greeting cards. This process enables the child to visualize and learn more about good dental hygiene and more about his or her tooth loss each time he or she removes a sticker from the proper position on the poster and places it on the greeting card.

The purpose of the present invention is to stimulate children's interest in the mythological "Tooth Fairy," provide knowledge concerning the anatomy of the mouth as well as teach about good oral hygiene. In use, the parent receives the assembly, hangs the poster on the child's wall or door prior to that child losing his or her first tooth. The parent hides the greeting cards in a safe place out of the child's reach. When the child's first tooth is lost, the parent gives the child the pouch into which the child places the lost tooth. Then, when the child is asleep, the parent takes the tooth out of the pouch and replaces it with the first greeting card and a gift or a nominal amount of money. The pouch allows the parent, a.k.a. the mythological "Tooth Fairy," to easily find the tooth beneath the child's pillow.

The greeting cards are numbered sequentially so as to track the order of tooth loss. For example, the first greeting card is given when the first tooth falls out, the second greeting card is given when the second tooth falls out, and so on. On the front cover or outside of each greeting card there can be printed matter such as pictures of various child-like activities, that is, children brushing their teeth bedtime, praying or playing. These are but examples of the myriad of child-like activities which can be depicted on the card. On the inside of the card, there may be indicia in the form of text such as a poem purposed to educate children about good dental hygiene and provide information concerning various aspects of the mouth. The inside of the card may further include indicia combined with appropriate arranged blank spaces, the spaces allowing the child to write his or her name, age, the type of tooth lost by the child, and the function of the tooth.

The drawstring bag used in the present invention is made up of a flexible material, such as a thermoplastic film or other suitable fabric material. The bag has a mouth and an open-ended tubular channel formed transversely along the peripheral wall of the bag adjacent of the mouth. A string, cord or tape is passed once through the channel. Both ends of the string, cord or tape can be joined to each other to form an endless loop. The loop may be draw to gather the fabric material adjacent the mouth and thus, close the mouth of the bag.

Accordingly, it is a principal object to stimulate children about the mythological "Tooth Fairy," provide knowledge concerning the anatomy of the mouth, and teach about good oral hygiene.

It is another object to assemble an apparatus which is relatively easy and simple to operate and which may be economically fabricated.

It is a further object to stimulate a parent-child relationship.

Still another object to provide an assembly which makes learning about teeth and dental hygiene both fun and exciting to the child.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
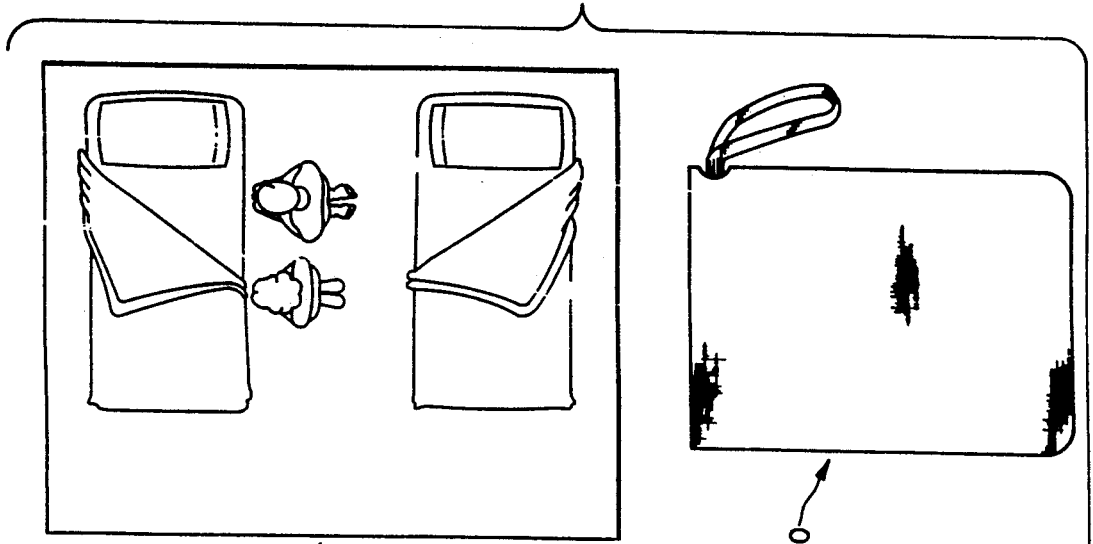
FIG. 1 an environmental elevational view of the educational dental kit in accordance with the present invention.
Figure 1:
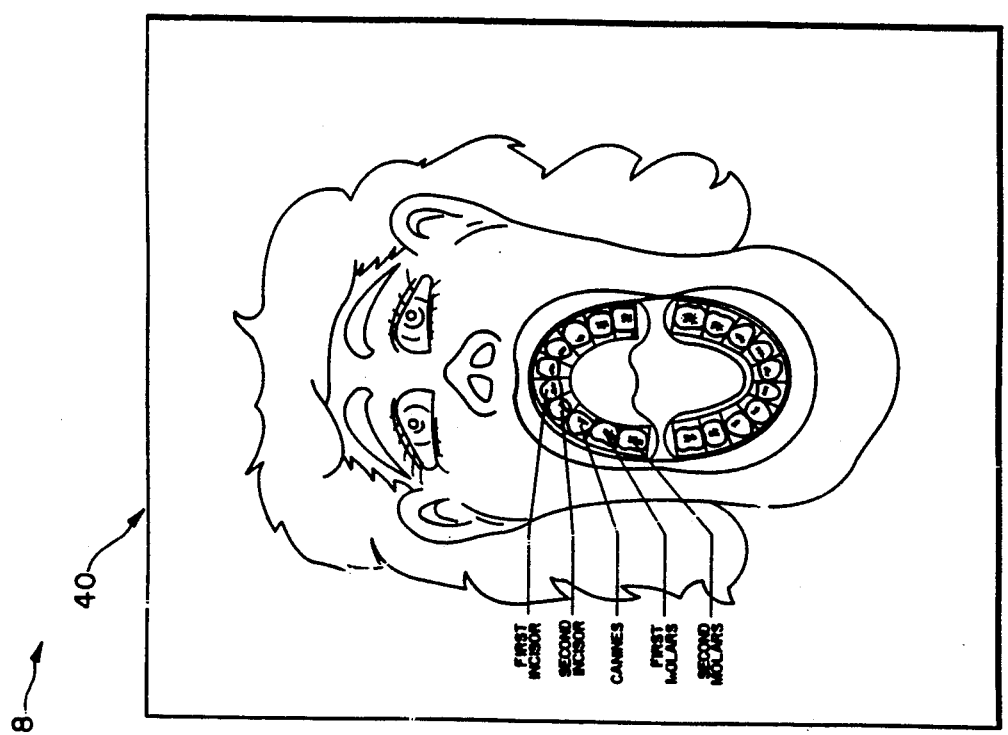

Now referring to the drawings and more particularly to FIG. 1, there is shown an embodiment of the educational dental kit or assembly 8 for entertaining and educating young children about both the mythological "Tooth Fairy" and good dental hygiene. The present invention as illustrated in FIG. 1 is made up of a greeting card 10, a poster 40, and a drawstring pouch 30.

Figure 2:
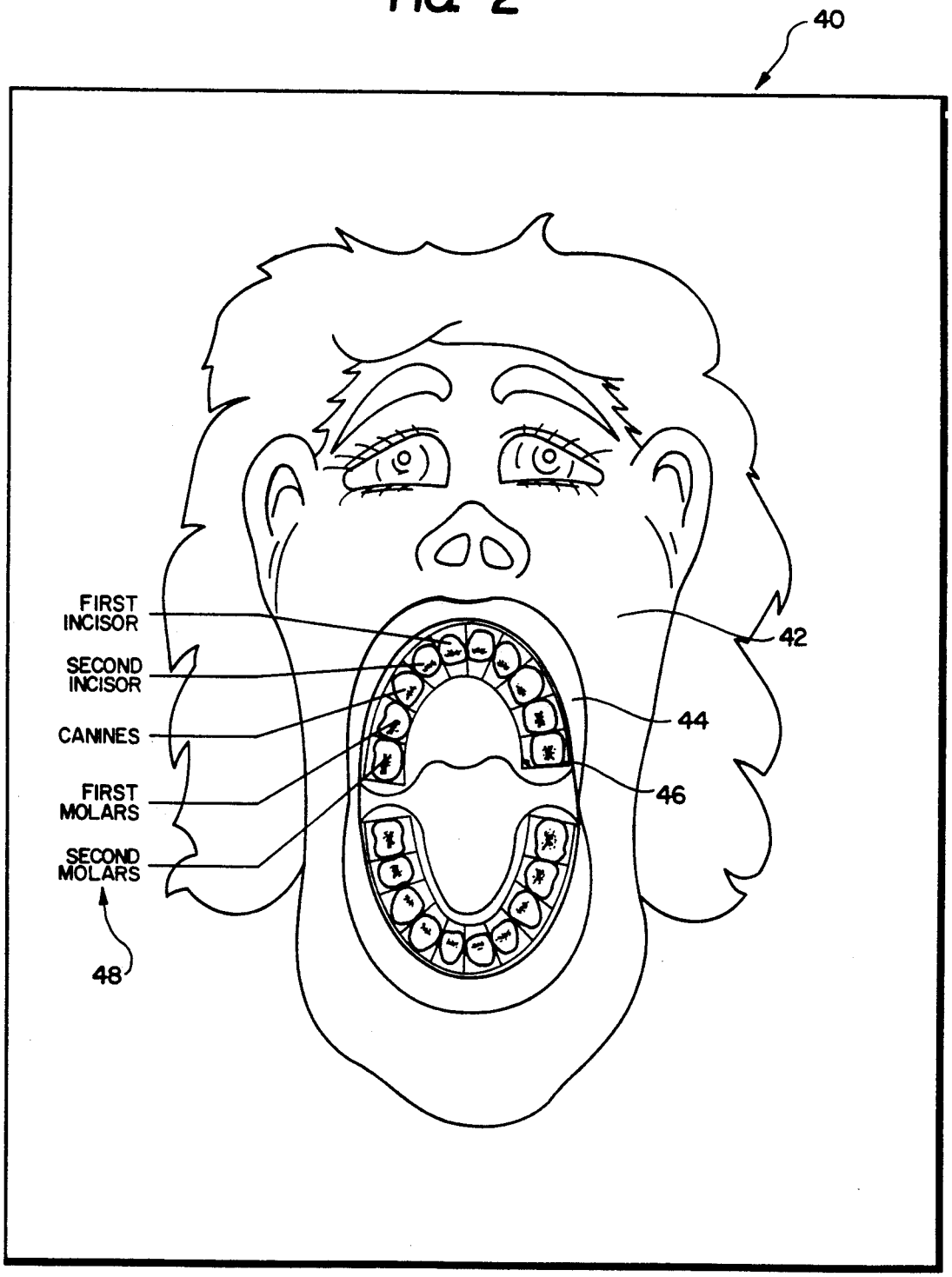
FIG. 2 is an environmental plan view of the front surface of the poster which is included as a component part of the present invention as shown in FIG. 1.

Referring to FIG. 2, the poster 40 is shown having printed upon it a child's face 42 with particular emphasis on a mouth 44 which may contain removable stickers 46. Each removable sticker 46 represents a different tooth in the child's mouth. When the child loses a tooth, a corresponding sticker 46 is removed from the respective location in the mouth on the poster 40 and is placed in the appropriate location 26 in the greeting card 10.

Indicia 48 describing each type of tooth in a child's mouth and/or the tooth's function, and describing the proper dental hygiene may be located throughout the poster 40. The indicia 40 is arranged in such a manner as to facilitate rapid and comprehensive understanding by a child. It will also create an entertaining as well as educational atmosphere.

Figure 3:
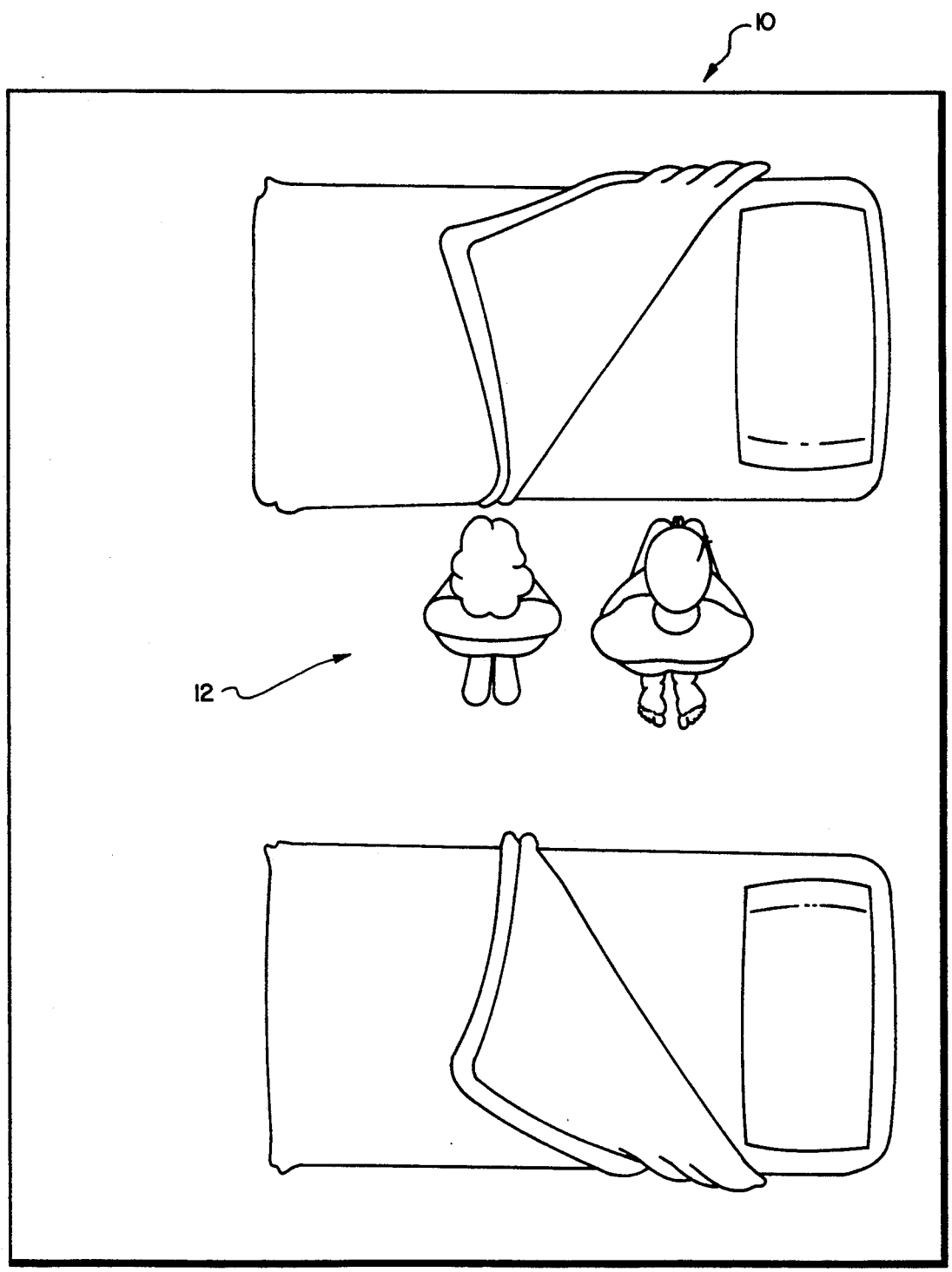
FIG. 3 illustrates an environmental plan view of the front outside surface of the greeting card which is included as an element of the present invention as shown in FIG. 1.

Another important aspect of the child's educational development is through the use of greeting cards 10. One such greeting card is 10 shown in FIGS. 3 and 4. The greeting card 10 may include a pictorial representation 12 located on the front outside surface thereof which may represent a child-like activity such as children brushing their teeth before bedtime, children playing outside with friends, or children praying at their bedside as shown in FIG. 3. However, these are mere examples and are not intended to limit the scope of the invention.

Figure 4:
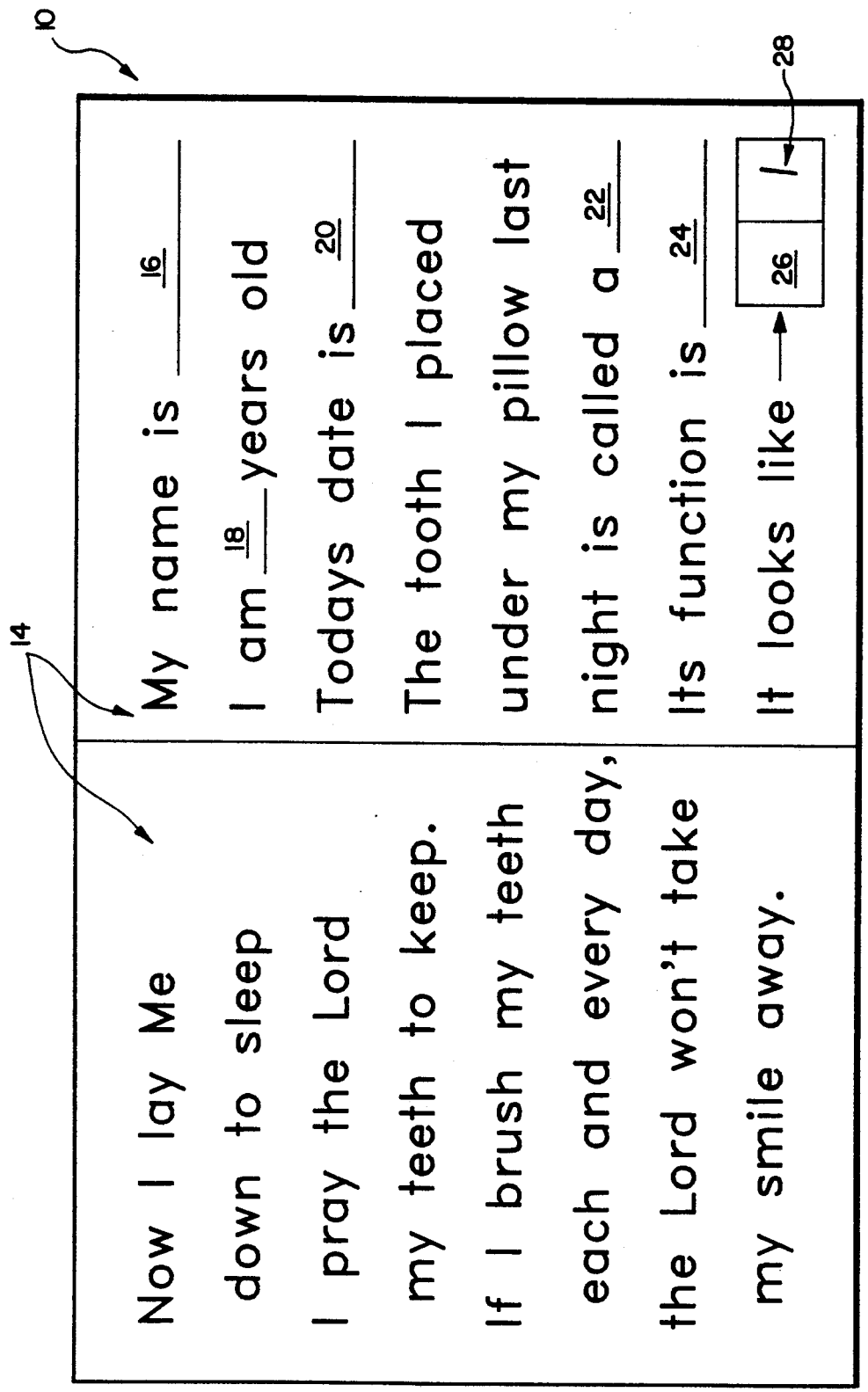
FIG. 4 illustrates an environmental plan view of the inside surface of the greeting card shown in FIG. 1 showing both right and left sides of the greeting card when the card is unfolded in an open posture.

On the inside surface of the greeting card 10, as shown in FIG. 4, there is space provided for indicia 14 such as the text representing an educational poem. The purpose of the indicia 14 is to entertain and stimulate good oral hygiene in the child. On the opposite side of the greeting card 10 there is included means to encourage active participation of the child such as a plurality of spaces in which the child may write his or her name 16, age 18, date that the tooth fell out 20, name of the tooth that fell out 22, function of the tooth that fell out 24, as well as an area 26 for the child to place the sticker 46 representing the child's lost tooth.

A number 28 corresponding to the order in which each a tooth is lost may also be provided inside each greeting card 10. The number 28 would appear in ascending order in each successive greeting card 10. The first time a tooth is lost, the child should receive card number 1. When the second tooth is lost by the child, the second greeting card 10 should be presented, when the third tooth is lost, the third greeting card 10 should be presented, and so on.

Figure 5:
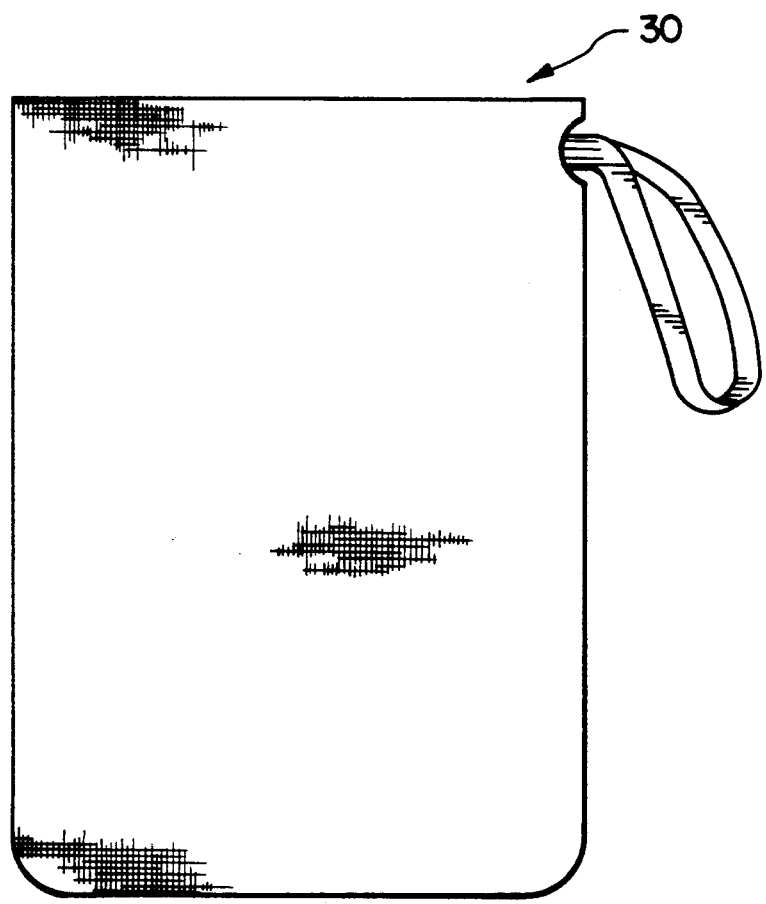
FIG. 5 is a front elevational view of the drawstring bag according to the present invention as shown in FIG. 1.

The drawstring bag 30 shown in FIG. 5 is also included in the assembly 8 to provide a way for the parent to quickly and efficiently located and retrieve the lost tooth such as when placed beneath the child's pillow just prior to the child retiring to bed. The bag or pouch 34 further provides a receptacle for the parent to replace the lost tooth with a gift such as a nominal amount of currency. The bag 10 may plan or may carry indicia such as a feminine or masculine pattern which could distinguish a boys bag from a girls bag.

It is to be understood that the present invention is not limited to the sole embodiment described above, but encompasses any and all embodiments within the scope of the following claims.

I claim:

1. An educational dental kit for use by children, said kit comprising:
   a drawstring pouch;
   a poster carrying a general representation of a human mouth, said mouth having a plurality of teeth, said poster also having a plurality if stickers arranged thereon, each one of said plurality of stickers having inscribed thereon a respective one of said plurality of teeth;
   a plurality of greeting cards each including a predetermined location for a placement of one of said plurality of stickers, whereby
   when a tooth of the child is lost, a respective one of said plurality of stickers which corresponds to the lost tooth is removed from said poster and is placed on said predetermined location on one of said plurality of greeting cards; and further whereby
   when a tooth of the child is lost, said the lost tooth is placed in said pouch and said pouch is place beneath a pillow prior to the child falling asleep on the pillow; and after the child falls asleep on the pillow, said pouch is removed from beneath the pillow, the tooth is removed from said pouch and is replace by a gift and said first one of said plurality of greeting cards and said pouch is replaced beneath the pillow.

2. The educational kit according to claim 1, wherein said plurality of greeting cards each further include means to maintain an order in which each one of said plurality of stickers are removed from said poster, whereby
   said order in which each one of said plurality of stickers are removed from said poster represents an order in which the lost tooth is lost from the mouth of the child.

3. The educational kit according to claim 2, wherein said means to maintain an order in which each one of said plurality of stickers are removed from said poster includes a number appearing on each one of said plurality of greeting cards, whereby
   said number on each successive one of said plurality of greeting cards appears in an ascending order.

4. The educational kit according to claim 1, wherein said plurality of greeting cards each further include means to receive variable information.

5. The educational kit according to claim 4, wherein said means to receive variable information includes a predetermined location for a placement of a name of the child.

6. The educational kit according to claim 4, wherein said means to receive variable information includes a predetermined location for a placement of an age of the child.

7. The educational kit according to claim 4, wherein said means to receive variable information includes a predetermined location for a placement of a date on which the child lost a tooth.

8. The educational kit according to claim 4, wherein said means to receive variable information includes a predetermined location for a placement of a name of the lost tooth of the child.

9. The educational kit according to claim 1, wherein said poster further includes indicia correspondingly describing each one of said plurality of teeth as well as a proper oral hygiene of the same, whereby said indicia has educational value.

10. The educational kit according to claim 1, wherein said greeting card further includes indicia in the form of a picture, whereby
    said indicia in the form of a picture represents a child-like activity.

11. The educational kit according to claim 1, wherein said greeting card further includes indicia in the form of text, whereby said indicia has educational value.

12. The educational kit according to claim 11, wherein each of said plurality of greeting cards includes a fold, each of said plurality of greeting cards being foldable along said fold to open and close each of said plurality of greeting cards into an open and closed position, respectively.

13. The educational kit according to claim 12, wherein each of said plurality of greeting cards includes a front outside surface, a left and right inside surface, and a rear outside surface.

14. The educational kit according to claim 13, further including indicia on said right inside surface, whereby
    said indicia on said right inside surface is visible only when said card is in said open position.

15. The educational kit according to claim 13, further including indicia on said left inside surface, whereby
    said indicia on said right inside surface is visible only when said card is in said open position.

* * * * *